US009726578B2

(12) United States Patent
Miller (10) Patent No.: US 9,726,578 B2
(45) Date of Patent: Aug. 8, 2017

(54) METHODS AND SYSTEMS FOR PARTICLE COLLECTION AND ANALYSIS

(71) Applicant: The Boeing Company, Huntingon Beach, CA (US)

(72) Inventor: Jeffrey L. Miller, Mukilteo, WA (US)

(73) Assignee: The Boeing Company, Chicago, IL (US)

( * ) Notice: Subject to any disclaimer, the term of this patent is extended or adjusted under 35 U.S.C. 154(b) by 462 days.

(21) Appl. No.: 14/311,655

(22) Filed: Jun. 23, 2014

(65) Prior Publication Data

US 2015/0369706 A1 Dec. 24, 2015

(51) Int. Cl.
*G01N 1/22* (2006.01)
*G01N 15/02* (2006.01)
*G01N 15/00* (2006.01)
*G01N 15/06* (2006.01)

(52) U.S. Cl.
CPC ......... *G01N 1/2205* (2013.01); *G01N 1/2226* (2013.01); *G01N 15/02* (2013.01); *G01N 15/06* (2013.01); *G01N 2001/2223* (2013.01); *G01N 2001/2241* (2013.01); *G01N 2015/0046* (2013.01)

(58) Field of Classification Search
None
See application file for complete search history.

(56) References Cited

U.S. PATENT DOCUMENTS

| 3,473,388 | A | * | 10/1969 | Lynn | G01N 1/2035 73/863.03 |
| 3,625,065 | A | * | 12/1971 | Thompson | G01N 1/2035 73/863.51 |
| 4,201,256 | A | * | 5/1980 | Truhan | B01D 45/12 144/252.2 |
| 4,832,717 | A | * | 5/1989 | Peters | B08B 15/023 454/187 |
| 4,967,608 | A | * | 11/1990 | Yost | B01L 1/04 377/10 |
| 6,062,092 | A | | 5/2000 | Weaver | |

(Continued)

OTHER PUBLICATIONS

Pilot, G. et al., "Measurement of secondary emissions during laser cutting of steel equipments," Nuclear Engineering and Design, Amsterdam, NL, vol. 238, No. 8, Aug. 1, 2008, pp. 2124-2134.

(Continued)

*Primary Examiner* — Robert R Raevis
(74) *Attorney, Agent, or Firm* — Armstrong Teasdale LLP (57) ABSTRACT

An example method for collection and analysis of particles from a particle generating source enclosed within an enclosure having an inlet and an outlet is described. The method includes supplying filtered air into the enclosure through the inlet, extracting, with a vacuum source, an aerosol stream including particles from the particle generating source through the outlet, directing the aerosol stream from the outlet of the enclosure to the vacuum source via a sampling tower. The sampling tower includes at least one nozzle for s

(56) References Cited

U.S. PATENT DOCUMENTS

| | | |
|---|---|---|
| 6,412,358 B1 | 7/2002 | Gatov |
| 2006/0060006 A1 | 3/2006 | Ornath |
| 2010/0116261 A1* | 5/2010 | Fairweather ....... B23Q 11/0046 125/13.01 |

OTHER PUBLICATIONS

Gonzalez et al., "Metal particles produced by laser ablation for ICP-MS measurements," Talanta, Elsevier, Amsterdam, NL, vol. 73, No. 3, Sep. 6, 2007, pp. 567-576.

J. Koch, et al., "Particle size distributions and compositions of aerosols produced by near-IR femto- and nanosecond laser ablation of brass," Journal of Analytical Atomic Spectrometry, vol. 19, No. 2, Jan. 1, 2004, p. 267.

Jan Kosler, et al., "Chemical and phase composition of particles produced by laser ablation of silicate glass and zircon implications for elemental fractionation during ICT-MS analysis." Journal of Analytical Atomic Spectrometry, vol. 20, No. 5, Jan. 1, 2005, p. 402.

European Search Report issued in European Application No. 1569476 on Oct. 23, 2015.

"Characterization of graphite composite material particulates from United States Air Force Aircraft Maintenance Operations," Thesis, Richard E. Yon, Captain, USAF, BSC, AFIT/GIH/ENV/11-M04, Department of the Air Force, Air University, Air Force Institute of Technology, Wright-Patterson Air Force, Base, OH, Approved for Public Release, Distribution unlimited, Mar. 2011.

Cena, Lorenzo, G., et al. "Characterization and Control of Airborne Particles Emitted During Production of Epoxy/Carbon Nanotube Nanocomposites," Journal of Occupational and Environmental Hygiene, vol. 8 (2011) pp. 86-92.

Bello, Dhimiter, et al., "Exposure to nanoscale particles and fibers during machining of hybrid advanced composites containing carbon nanotubes," J Nanoparticle Research, DOI 10.1007/s11051-008-9499-4, Aug. 22, 2008.

Haddad, Madjid, et al., "Surface quality and dust analysis in high speed trimming of CFRP," Applied Mechanics and Materials vol. 232 (2012), pp. 57-62.

Haddad, Madjid, et al., "Influence of tool geometry and machining parameters on the surface quality and the effect of surface quality on compressive strength of carbon fibre reinforced plastic," Materials Science Forum, vol. 763 (2013), pp. 107-125.

Brouwer, Derk, "Exposure to manufactured nanoparticles in different workplaces," Toxicology, vol. 269 (2010), pp. 120-127.

Centers for Disease Control and Prevention, Niosh Publication No. 2013-145 "Occupational Exposure to Carbon Nanotubes and Nanofibers", Current Intelligence Bulletin 65; http://www.cdc.gov/niosh/docs/2013-145/.

Ramulu, M., et al., "Machining of Fiber Reinforced Composites: Review of Environmental and Health Effects," International Journal of Environmentally Conscious Design & Manufacturing, vol. 11, No. 4 (2004).

* cited by examiner

METHODS AND SYSTEMS FOR PARTICLE COLLECTION AND ANALYSIS

BACKGROUND

The field of the disclosure relates to methods and systems for collection and analysis of particles from a machining process.

Dry (i.e., without coolant) drilling, milling, grinding, and other machine processing of many materials produces dust particles. The produced dust particles may vary in size between different materials, during a single operation on a single material, between different types of operations on a material, between different cutting tools, etc. Particles from machining of some known materials may include, among other sizes, particles that are ultrafine and can be respirated.

Some known systems perform open air sampling of particles in the air around a particle generating device. The distance and location of the detection instruments relative to the particle source may significantly impact the results of particle analysis in such systems. Moreover, if the particle-producing device being studied is used with an activated dust extraction system, the results of such sampling do not accurately represent the particles produced by the device. However, if the particle-producing device is studied without activating the devices dust extraction system, the area around the device may be contaminated with dust from the particle-producing device.

BRIEF DESCRIPTION

One aspect of the present disclosure is a system for use in particle collection and analysis. The system includes an enclosure, a filter, a vacuum source, and a sampling tower. The enclosure is configured to be attached to a particle producing device and includes an inlet and an outlet. The filter is configured to be coupled to the inlet of the enclosure and configured to filter air directed to the enclosure through the inlet. The vacuum source is configured to be coupled in flow communication with the outlet of the enclosure to generate an aerosol stream from the enclosure to the vacuum source. The aerosol stream includes particles produced by the particle producing device. The sampling tower is configured to be coupled between the vacuum source and the enclosure outlet. The sampling tower includes at least one sampling nozzle extending into the sampling tower and configured for use sampling the aerosol stream from the enclosure to the vacuum source.

Another aspect of the disclosure is a method for collection and analysis of particles from a particle generating source enclosed within an enclosure having an inlet and an outlet. The method includes supplying filtered air into the enclosure through the inlet, extracting, with a vacuum source, an aerosol stream including particles from the particle generating source through the outlet, directing the aerosol stream from the outlet of the enclosure to the vacuum source via a sampling tower. The sampling tower includes at least one nozzle for sampling the aerosol stream. The method includes detecting, with a detection instrument coupled to the nozzle, at least one characteristic of the particles in the aerosol stream, and outputting data concerning the detected characteristic of the particles in the aerosol stream to a computing device.

In another aspect, a closed system for use in collection and analysis of particles produced at a particle producing location of a particle producing device includes an enclosure, a filter, a first vacuum source, and a sampling tower. The enclosure is attached to a particle producing device. The enclosure and the particle producing device cooperatively create a substantially sealed volume around the particle producing location. The enclosure includes an inlet to the sealed volume and an outlet from the sealed volume. The filter is coupled to the inlet of the enclosure and configured to filter air directed to the enclosure through the inlet. The first vacuum source has an inlet and an outlet. The first vacuum source inlet is coupled in flow communication with the enclosure outlet to generate an aerosol stream from the enclosure to the first vacuum source. The aerosol stream includes particles produced by the particle producing device. The first vacuum source outlet is coupled in flow communication with the filter to provide filtered air to the enclosure. The sampling tower is coupled between the first vacuum source inlet and the enclosure outlet. The sampling tower includes a plurality of sampling nozzles extending into the sampling tower and configured for sampling the aerosol stream from the enclosure to the vacuum source.

The features, functions, and advantages that have been discussed can be achieved independently in various embodiments or may be combined in yet other embodiments further details of which can be seen with reference to the following description and drawings.

DETAILED DESCRIPTION

The subject matter described herein relates to particles produced by an industrial process. More particularly, the subject matter relates to methods and systems for particle collection and analysis.

As used herein, an element or step recited in the singular and proceeded with the word "a" or "an" should be understood as not excluding plural elements or steps unless such exclusion is explicitly recited. Furthermore, references to "one implementation" of the present invention or the "exemplary implementation" are not intended to be interpreted as excluding the existence of additional implementations that also incorporate the recited features.

Figure 1:
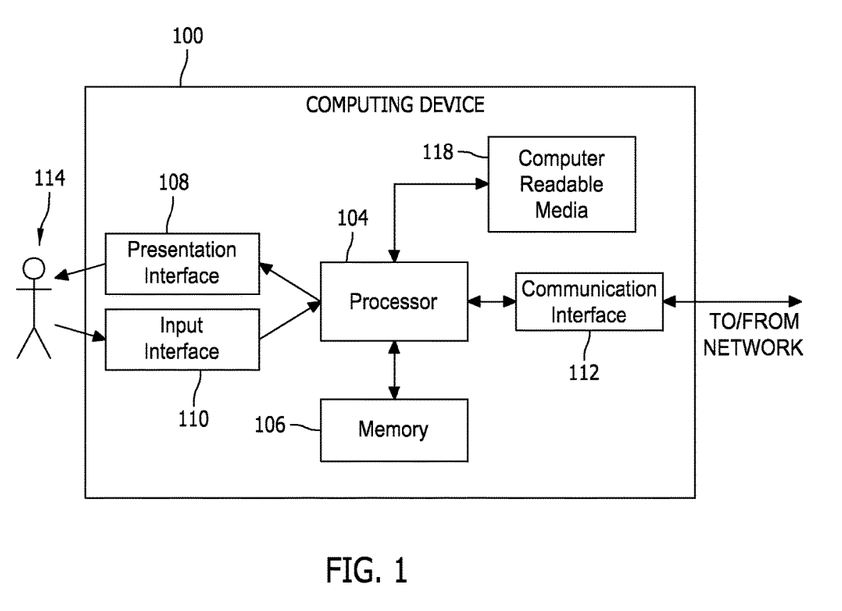
FIG. 1 is a block diagram of a computing device.

The example methods and systems described herein may be implemented with and/or may include one or more controllers. The controllers may include any suitable combination of analog and/or digital controllers capable of performing as described herein. In some implementations, the controller includes a computing device. FIG. 1 is a block diagram of an exemplary computing device 100 that may be used in a system for estimating propellant transfer. In the exemplary implementation, computing device 100 includes a memory 106 and a processor 104 that is coupled to memory 106 for executing programmed instructions. Processor 104 may include one or more processing units (e.g., in a multi-core configuration). Computing device 100 is programmable to perform one or more operations described herein by programming memory 106 and/or processor 104. For example, processor 104 may be programmed by encoding an operation as one or more executable instructions and providing the executable instructions in memory device 106.

Processor 104 may include, but is not limited to, a general purpose central processing unit (CPU), a microcontroller, a reduced instruction set computer (RISC) processor, an application specific integrated circuit (ASIC), a programmable logic circuit (PLC), and/or any other circuit or processor capable of executing the functions described herein. The methods described herein may be encoded as executable instructions embodied in a computer-readable medium including, without limitation, a storage device and/or a memory device. Such instructions, when executed by processor 104, cause processor 104 to perform at least a portion of the methods described herein. The above examples are exemplary only, and thus are not intended to limit in any way the definition and/or meaning of the term processor.

Memory device 106, as described herein, is one or more devices that enable information such as executable instructions and/or other data to be stored and retrieved. Memory device 106 may include one or more computer-readable media, such as, without limitation, dynamic random access memory (DRAM), static random access memory (SRAM), a solid state disk, and/or a hard disk. Memory device 106 may be configured to store, without limitation, maintenance event log, diagnostic entries, fault messages, and/or any other type of data suitable for use with the methods and systems described herein.

In the exemplary implementation, computing device 100 includes a presentation interface 108 that is coupled to processor 104. Presentation interface 108 outputs (e.g., display, print, and/or otherwise output) information such as, but not limited to, installation data, configuration data, test data, error messages, and/or any other type of data to a user 114. For example, presentation interface 108 may include a display adapter (not shown in FIG. 1) that is coupled to a display device, such as a cathode ray tube (CRT), a liquid crystal display (LCD), a light-emitting diode (LED) display, an organic LED (OLED) display, and/or an "electronic ink" display. In some implementations, presentation interface 108 includes more than one display device. In addition, or in the alternative, presentation interface 108 may include a printer.

In the exemplary implementation, computing device 100 includes an input interface 110 that receives input from user 114. For example, input interface 110 may be configured to receive selections, requests, credentials, and/or any other type of inputs from user 114 suitable for use with the methods and systems described herein. In the exemplary implementation, input interface 110 is coupled to processor 104 and may include, for example, a keyboard, a card reader (e.g., a smartcard reader), a pointing device, a mouse, a stylus, a touch sensitive panel (e.g., a touch pad or a touch screen), a gyroscope, an accelerometer, a position detector, and/or an audio input interface. A single component, such as a touch screen, may function as both a display device of presentation interface 108 and as input interface 110.

In the exemplary implementation, computing device 100 includes a communication interface 112 coupled to memory 106 and/or processor 104. Communication interface 112 is coupled in communication with a remote device, such as another computing device 100, a remote sensor, a detection instrument, etc. For example, communication interface 112 may include, without limitation, a wired network adapter, a wireless network adapter, an instrument input port, and/or a mobile telecommunications adapter.

Instructions for operating systems and applications are located in a functional form on non-transitory memory 106 for execution by processor 104 to perform one or more of the processes described herein. These instructions in the different implementations may be embodied on different physical or tangible computer-readable media, such as memory 106 or another memory, such as a computer-readable media 118, which may include, without limitation, a flash drive, CD-ROM, thumb drive, floppy disk, etc. Further, instructions are located in a functional form on non-transitory computer-readable media 118, which may include, without limitation, a flash drive, CD-ROM, thumb drive, floppy disk, etc. Computer-readable media 118 is selectively insertable and/or removable from computing device 100 to permit access and/or execution by processor 104. In one example, computer-readable media 118 includes an optical or magnetic disc that is inserted or placed into a CD/DVD drive or other device associated with memory 106 and/or processor 104. In some instances, computer-readable media 118 may not be removable.

Figure 2:
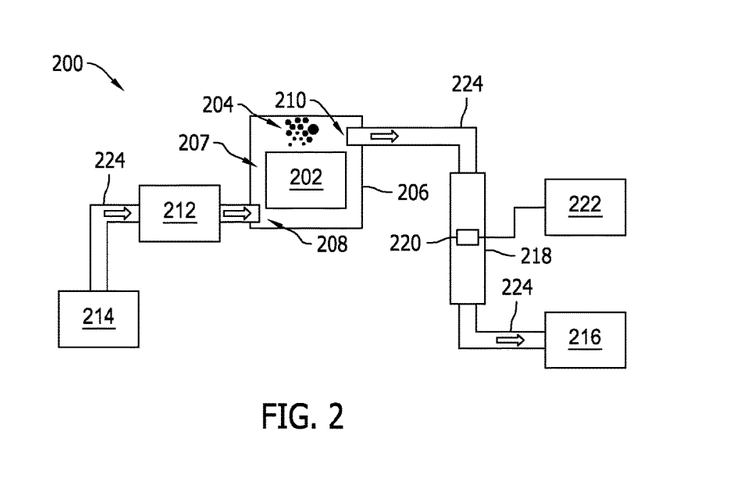
FIG. 2 is a block diagram of a system for collection and analysis of particles produced by a particle-producing device.

FIG. 2 is a simplified diagram of an example implementation of a system 200 for use in particle collection and analysis. The system 200 is used to collect and/or analyze particles from a particle producing device 202.

Particle producing device 202 is any device the produces, generates, or otherwise is a source of a particle or particles 204 of interest. For example, in some implementations, particle producing device 202 is a manufacturing tool (e.g., a saw, a milling machine, a drill, a multi-axis machine tool, a machining center, a portable drilling system, a grinding center, etc.) that cuts, drills, mills, routs, shapes, grinds, machines, etc. a work piece. The process performed by particle producing device 202 removes some of the material of which the work piece is made creating particles 204 (e.g., dust). In other implementations, particle producing device 202 is any other device that produces particles 204 that may be collected and/or analyzed. Particles 204 may be a byproduct of the process performed by particle producing device 202 or may themselves be the end product of the process performed by particle producing device 202. System 200 specifically collects particles from a particle generating source (not shown in FIG. 2) of particle producing device 202. For example, if particle producing device 202 is a saw, the particle generation source is the saw blade. The location of particle generation (also referred to as the particle production location) is the location of the particle source on/in the particle producing device 202.

System 200 includes an enclosure 206 attached to particle producing device 202. In FIG. 2, enclosure 206 substantially surrounds particle producing device 202. In other implementations, enclosure 206 substantially surrounds the location of particle generation by, for example, surrounding the particle source or a volume of space surrounding the particle source. The enclosure 206 may substantially surround the location of particle generation by itself, or cooperatively with one or more portions of particle producing device 202, another structure (such as a wall or floor), or another device. For example, enclosure 206 and a table (not shown in FIG. 1) of particle producing device 202 may cooperatively define a substantially sealed volume enclosing the particle source.

Enclosure 206 may be made of any suitable material for substantially enclosing a volume around the location of particle generation. For example, enclosure 206 may be made of wood, metal plastic, rubber, glass, fiberglass, acrylic materials, laminated materials, etc. Moreover, enclosure 206 may be made of a combination of materials. For example, a portion of enclosure 206 may be made of a rigid or semi-rigid material, while another portion of enclosure 206 is made of a flexible material. In particular, some implementations include a flexible portion in the enclosure to permit the enclosure to move with a moving component of particle producing device 202, such as a cutter head, an X-Y table, etc. The flexible portion may be specifically configured for the type of machine being studied. For example, a different configuration may be used for a two dimensional device with a fixed cutter and a moving work piece table that would be used for a drill press with a bit (cutter) that moves relative to a fixed work piece. Moreover, the amount of movement of a work piece, cutter, or other components of particle producing device 202 may affect the desired configuration of enclosure 206.

Enclosure 206 includes an inlet 208 and an outlet 210. Outlet 210 includes a nozzle (not shown in FIG. 2) for extracting particles 204 from enclosure 206. In the exemplary implementation, the nozzle is a flexible, anti-static nozzle that is positioned close to the particle source to provide efficient particle removal. Any suitable type of nozzle, including a nozzle integral to particle producing device 202 may be used. Other implementations do not include a nozzle. Particle counters or "sniffers" (not shown) can be used to verify the efficiency of capture through the nozzle. Inlet 208 is coupled to a filter 212 to supply filtered air into a volume 207 (only two dimensions of which are shown in FIG. 2) defined, at least in part by enclosure 206. In the exemplary implementation, filter 212 is a high-efficiency particulate air (HEPA) filter. In other implementations, filter 212 may be any other suitable filter for providing filtered air to enclosure 206. A blower 214 is coupled in flow communication with inlet 208 via filter 212 to provide the filtered air to enclosure 206. In the exemplary implementation, blower 214 is a blower output of a vacuum device, such as a shop vacuum. Alternatively, blower 214 may be a dedicated blower or any other device suitable for providing a stream of air into the volume 207 defined by enclosure 206. In some implementations, blower 214 also includes a built in filter, which can be a HEPA filter or any other suitable type of filter, configured and coupled to filter the air exhausted by blower 214.

A vacuum source 216 is coupled in flow communication with the outlet 210 to extract air and particles 204 from inside enclosure 206 to generate a stream (e.g., an aerosol stream or flow of air and/or particles 204) from enclosure 206 to vacuum source 216. In the exemplary implementation, vacuum source 216 is a vacuum, such as a shop vacuum. Alternatively, vacuum source may be any other suitable source of vacuum and/or airflow. In some implementations, vacuum source, 216 also includes a filter, which may be a HEPA filter or any other suitable type of filter, configured and coupled to filter its exhaust air.

A sampling tower 218 is coupled between vacuum source 216 and outlet 210 such that the stream from enclosure 206 to vacuum source 216 passes through sampling tower 218. Sampling tower 218 is made of a conductive pipe or tube (e.g. aluminum) having a circular cross section of a known constant diameter, such as between 4 and 10 inches. In other implementations, sampling tower 218 may have any other suitable diameter, whether larger or smaller, and/or may be made from any other suitable material. Moreover, in some implementations, sampling tower 218 has a cross-section that is not circular. Sampling tower 218 is vertically oriented to facilitate movement of larger particles (sometimes referred to as "boulders"), e.g. greater than about 50 micrometers, to vacuum source 216 by gravity. In other implementations, sampling tower 218 is horizontally oriented.

Sampling tower 218 includes a nozzle 220 that extends into sampling tower 218 to permit sampling of the stream from enclosure 206 to vacuum source 216. Although a single nozzle 220 is shown in FIG. 2, system 200 may include any suitable number of nozzles 220. In the exemplary implementation, nozzle 220 is an isokinetic nozzle. In other implementations, sampling tower 218 includes any other suitable type of nozzle. Nozzle 220 is positioned generally centered within sampling tower 218 and parallel with the flow direction of the stream from enclosure 206 to vacuum source 216, so that air and particles 204 in the stream may enter nozzle 220. In some implementations, sampling tower 218 includes one or more additional sensors or detectors, such as pitot tubes, differential pressure sensors, anemometers, etc.

Nozzle 220 is coupled to a detection system 222. The detection system 222 includes a detection instrument and/or a computing device (neither separately shown in FIG. 2). The detection instrument is any suitable detection instrument for use with nozzle 220, such as a cascade impactor, a particle counter, a mass concentration monitor, a single stage impactor, etc. The computing device may be, for example, computing device 100, or any other suitable computing device. Detection system 222 detects at least one characteristic of the stream and/or particles 204 within the stream. The detected characteristics can include concentration of particles 204 in the stream, sizes of particles 204, numbers of particles, concentrations of different size particles, masses of particles 204, composition of particles 204, etc.

To satisfy isokinetic sampling conditions, the velocity at nozzle 220 should equal the velocity in the sampling tower 218. This may be achieved in system 200 by measuring the velocity in tower 218 using pitot tubes or an equivalent method and selecting the correct diameter nozzle 220 determined by the flow rate of the detection instrument, generally between 0.7 and 28 lpm. In some embodiments, the flow rate (velocity) through the sampling tower 218 or the detection instrument is adjusted to achieve the required velocity in nozzle 220 for isokinetic sampling conditions.

The length 221 of sampling tower 218 is determined to facilitate isokinetic sampling conditions based on the required ratios of the nozzles 220 and/or the requirements of other sensors/detectors included in sampling tower 218. For example, for a pitot tube, it is suggested that sampling tower 218 have a length upstream of the pitot tube that is 8.5 times the diameter of the tower 218 and a length downstream that is at least 1.5 times the diameter of the tower 218. Thus, for a 4 inch diameter sampling tower 218, the minimum length 221 of sampling tower (based only on a pitot tube) is 40 inches.

Nozzles 220 permit, in conjunction with detection system 222, for direct reading, real-time monitoring of the characteristics of the stream from enclosure 206 to vacuum source 216 and/or particles 204. Additionally, nozzles 220 and detection system 222 may be used for later monitoring of characteristics the stream and particles 204. For example, collected data may be transferred to a computing device 100 for subsequent review or analysis. Moreover, some detection instruments may produce data that requires subsequent analysis or interaction (which may not be accomplished in real time) to produce data describing the characteristic being monitored by the detection instrument. The output of the analysis, e.g., the output of detection system 222, may include a normalized particle count distribution graph, a total counts and concentration graph, mass of collected material per filter (when multiple filters are used), a normalized particle mass distribution chart, an indoor air quality analysis, a particle size probability chart, and/or any other suitable analysis result.

Vacuum source 216, sampling tower 218, and outlet 210 are coupled together in flow communication by ducts 224. The exemplary ducts 224 are flexible, antistatic or conductive, vacuum hose. Conductive or anti-static vacuum ducts limit the likelihood of particles sticking to the walls of duct 224. Alternatively, any other suitable ducting may be used to guide the stream from enclosure 206 to vacuum source 216 via sampling tower 218.

In general, system 200 operates by capturing particles 204 using vacuum. Outlet 210 is configured to provide sufficient suction for representative operations to attempt to ensure that all or most particles 204 are collected. Enclosure 206 is positioned around the particle source and lightly pressurized with HEPA filtered purge air from blower 214 via filter 212. The filtered air maintains a purge in enclosure 206 to isolate outside contaminants so that only the generated particles 204 of interest are captured and subsequently analyzed. In some implementations, the air delivered into enclosure 206 is diffused, such as via a diffuser, so it does not interfere with particle extraction. The flow into enclosure 206 from blower 214 is approximately equal to the flow out of enclosure 206 to vacuum source 216 for balance. In implementations in which enclosure 206 includes a flexible portion, balancing the purge air and the vacuum flow rates facilitates maintaining enclosure 206 lightly inflated to avoid interference with operation of particle producing device 202. The generated particles 204 pass through the antistatic ducts 224 to isokinetic sampling tower 218. Some of the particles 204 in the stream are captured by nozzle 220 and provided to detection system 222, which determines at least one characteristic of the particles 204 and/or the stream.

Figure 3:
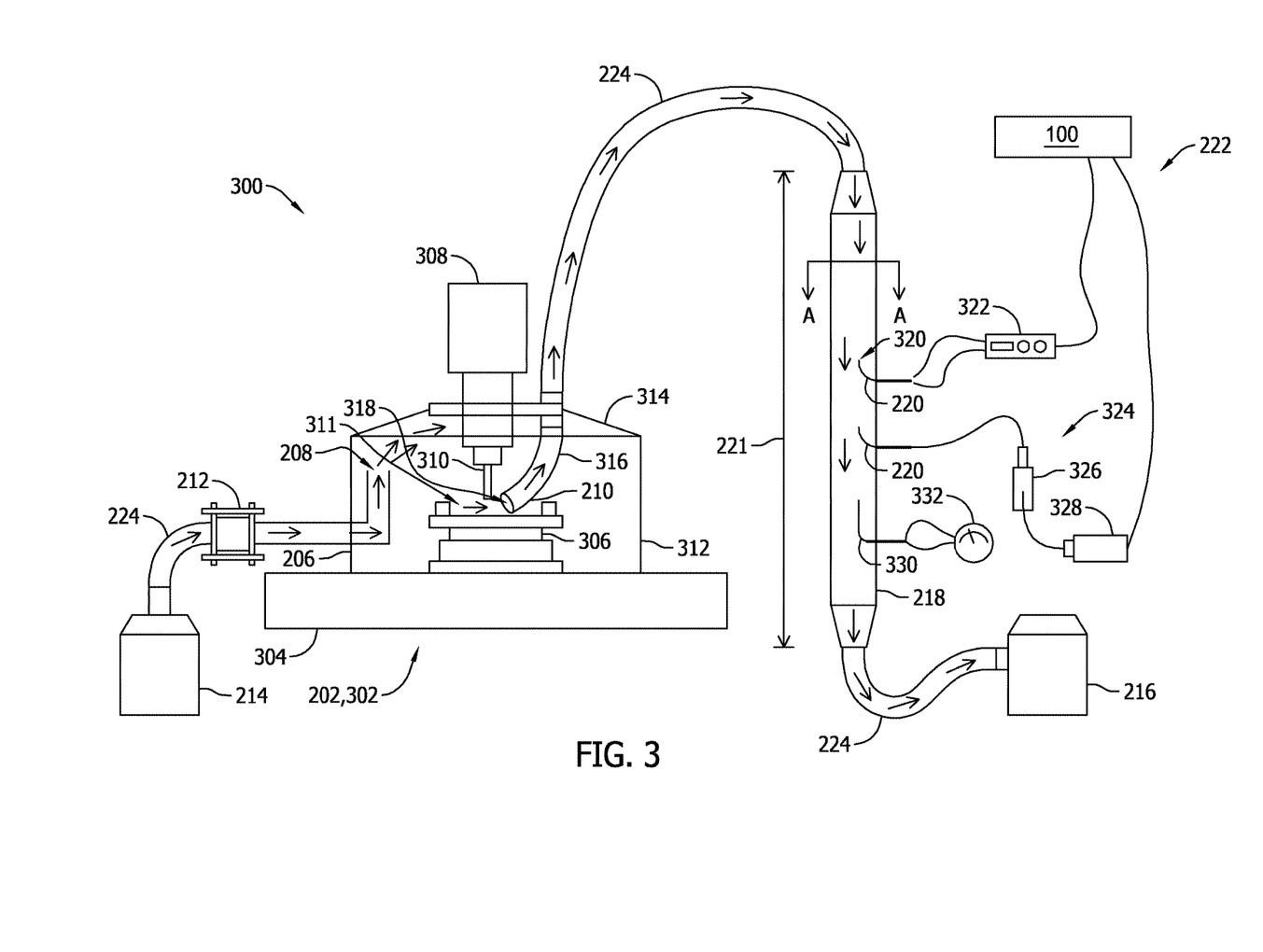
FIG. 3 is a diagram of an implementation of the system shown in FIG. 2.

FIG. 3 is a diagram of a system 300 for use in particle collection and analysis. System 300 is an implementation of system 200 described above. Similar components are identified by the same reference numerals. Except as otherwise described below, system 300 is similar to and functions the same as system 200.

In FIG. 3, particle producing device 202 is a three dimensional machining tool 302. Machining tool 302 has a work table 304 on which a work piece 306 is mounted. A z-axis column 308 with a cutting tool 310 mounted to it is positioned above work table 304. Cutting tool 310 is tool for cutting work piece 306, such as a drill bit, milling bit, etc. When cutting tool 310 operates (i.e., cuts) on work piece 306 particles of the material(s) from which work piece 306 is made are generated. Thus, cutting tool 310 may be considered a particle source and the area around cutting tool 310 may be considered a particle production location 311 (also referred to sometimes as a location of particle production generation). Work table 304 moves in the X and Y directions (left-right and in-out of the page as shown in FIG. 3) to move work piece 306 relative to the column 308 (and the cutting tool 310), which remains in a fixed position relative to the X and Y directions. The z-axis column 308 moves in the Z direction (up and down as shown in FIG. 3) to change the height of cutting tool 310 relative to work piece 306.

In the implementation shown in FIG. 3, enclosure 206 is mounted on machining tool 302. Enclosure 206 encloses volume 207 cooperatively defined by enclosure 206 and machining tool 302. More specifically, volume 207 is defined by enclosure 206, work table 304, and parts of column 308.

In FIG. 3, enclosure 206 has a first portion 312 and a second portion 314. In the exemplary implementation, first portion 312 is made of a substantially rigid material, such as a rigid plastic or acrylic material and second portion 314 is a flexible membrane. Alternatively, first portion 312 and second portion 314 may both be made from materials that are flexible. Enclosure 206 is firmly attached to machining tool 302 such that, except for inlet 208 and outlet 210, volume 207 is substantially sealed. The method of attachment and sealing may be varied to suit the particular particle producing device 202 and the particular installation desired (e.g., permanent vs. temporary/removable). For example, enclosure 206 may be mounted and or sealed to machining tool 302 using tape, glue, caulking, flexible sealant, screws/fasteners, welding, etc. The flexible second portion 314 permits the enclosure 206 to move and remain substantially sealed to machining tool 302 when column 308 and/or work table 304 move during an operation on work piece 306. The material for enclosure 206, and second portion 314 in particular, may be varied for different particle producing devices 202 with different directions of movement and amounts of movement to ensure enclosure 206 maintains a substantially sealed volume 207 around the particle production location 311. Moreover, as shown in FIG. 1, enclosure 206 may be sized to completely surround the particle producing device 202, which implementations may not need any flexible second portion 314.

Outlet 210 includes an adjustable outlet nozzle 316. Nozzle 316 is attached to z-axis column 308 and may be adjusted to vary its position relative to cutting tool 310. For example, nozzle 316 may be bent, turned, extended, retracted, etc. to vary the location of an opening 318 relative to the cutting tool 310. Because nozzle 316 is attached to column 308, nozzle 316 will move with column 308 and will maintain a substantially fixed relationship with cutting tool 310 and particle production location 311. Thus, the particle source does not change its distance from outlet nozzle 316, which may change the efficiency of particle collection. Outlet nozzle 316 may be attached to column 308 by any suitable fastener, including clamps, tape, screws/bolts, rivets, hook and loop fasteners, etc.

In the implementation shown in FIG. 3, sampling tower 218 includes two nozzles 220. Sampling tower 218 also includes a pitot tube 330 coupled to an external pressure gauge to detect the velocity of the stream including particles 204. Nozzles 220 extend into sampling tower 218 parallel to the direction of flow of the stream and with their openings 320 facing the oncoming stream of air and particles 204 (not shown in FIG. 3). The size of nozzles 220, including the diameter of openings 320, may be varied for particular detection instruments and to maintain isokinetic sampling conditions. Nozzles 220 are coupled to a detection system 222 that includes computing device 100 and two detection instruments 322 and 324. In the exemplary implementation, detection instrument 322 is a real-time detection instrument, such as a particle counter, a mass concentration detector, etc. Detection instrument 324 is a cascade impactor system including a cascade impactor 326 and a sampling pump 328. Detection instruments 322 and 324 provide their acquired and/or calculated data to computing device 100 for further processing, storage, and/or display to a user. Computing device 100 may be collocated with the rest of system 300, or may be remotely located and communicatively couple with detection instruments directly or via a network, such as a local area network, a wide area network, the Internet, etc. Other implementations do not include computing device 100. Moreover, in some implementations, detection instruments 322 and 324 may be integrated with computing device 100.

Figure 4:
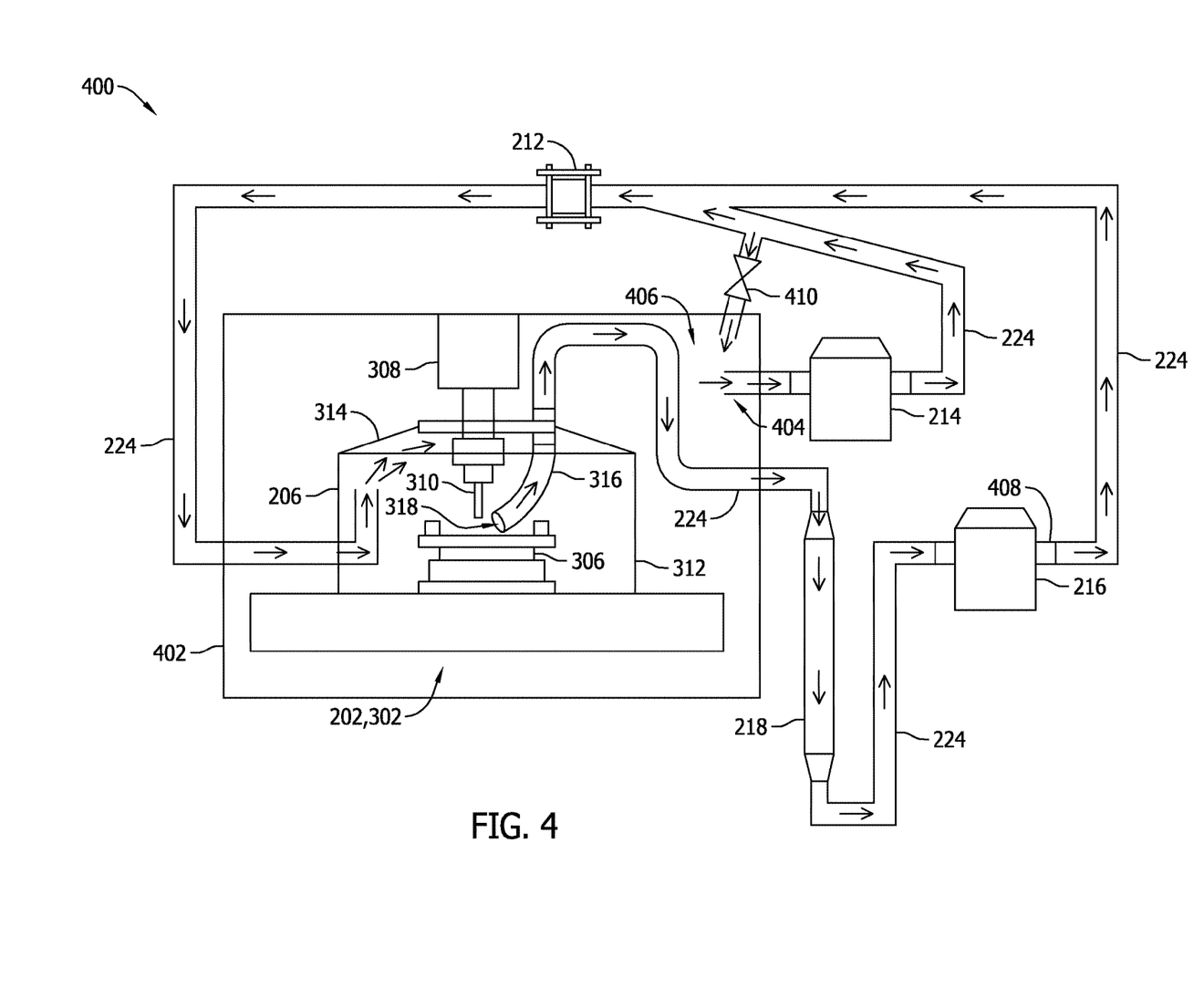
FIG. 4 is a diagram of another implementation of the system shown in FIG. 2.

FIG. 4 is a diagram of a closed system 400 for use in particle collection and analysis. System 400 is a closed loop implementation of system 200 described above. Moreover, in some implementations, system 400 is a self-contained system. Similar components are identified by the same reference numerals. Except as otherwise described below, system 400 is similar to and functions the same as systems 200 and 300, described above. For clarity nozzles 220, pitot tube 330, pressure gauge 332, detection system 222, and the components of detection system 222 are not shown in FIG. 4, but may be included in system 400.

System 400 includes enclosure 206 mounted to machining tool 302 in the same manner as system 300. Machining tool 302 and enclosure 206 are located within a larger enclosure 402. In the example implementation, enclosure 402 is a room within a building. In other implementations, enclosure 402 may be any substantially sealed enclosure capable of enclosing machining tool 302 and enclosure 206. Although blower 214, vacuum source 216, sampling tower 218, filter 212, and some of ducts 224 are shown outside of enclosure 402, they may also be positioned within enclosure 402.

In the illustrated implementation of FIG. 4, blower 214 includes an air intake 404 in flow communication with a volume 406 (only two dimensions of which are shown in FIG. 4) defined by enclosure 402. Enclosure 402 is an outer enclosure around enclosure 206 and serves as an inlet source for blower 214. Thus, the intake air that blower 214 outputs to enclosure 206, via filter 212, is taken from within enclosure 402. Moreover, in the exemplary implementation, vacuum source 216 provides additional blown air to enclosure 206 to supplement blower 214. Vacuum source 216 includes an output 408 that outputs (i.e., blows) air. Output 408 is coupled in flow communication with enclosure 206 via filter 212. In other implementations, blower 214 does not provide blown air to enclosure 206 and vacuum source 216 functions as both the vacuum source and the blower for system 400. In some implementations in which vacuum source 216 does not provide additional blown air to enclosure 206, output 408 is coupled in flow communication with volume 406. In such implementations, the inlet for blower 214 and the exhaust for vacuum source 216 are the same volume (i.e., volume 406), thus providing self-containment of system 400.

A balancing valve 410 is coupled between blower 214, vacuum source output 408, and filter 212 to balance the airflow to enclosure 206 and from volume 406. Balancing valve 410 prevents too much air being extracted from enclosure 402, which may lower the pressure within enclosure 402 to an unacceptable level, and prevents too much air from being supplied to enclosure 206, which may increase the pressure within enclosure 206 to an unacceptably high level. Moreover, the balancing valve 410 helps maintain the input flow to enclosure 206 at about the same rate as the outlet flow from enclosure 206.

Figure 5:
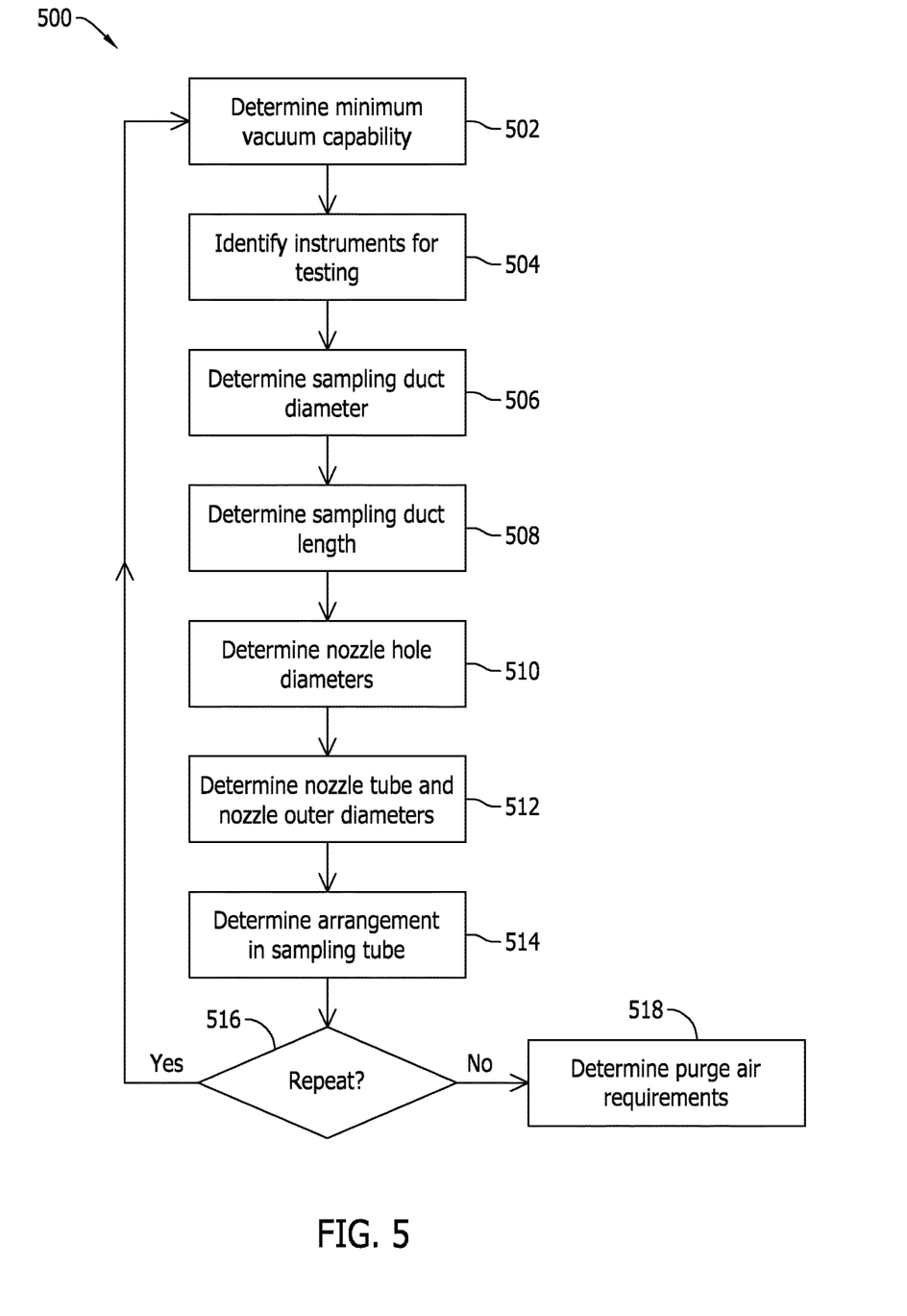
FIG. 5 is a flow diagram of a method for use in designing a system for collection and analysis of particles.

FIG. 5 is a flow chart of a method 500 of designing a system for use in particle collection and analysis, such as systems 200, 300, and/or 400. In particular, the method 500 is described with respect to a system using sampling tower 218 and/or ducts 224 with a round cross sectional geometry. Method 500 may be used for systems with ducts and sampling towers having different geometries (e.g., square, hexagonal, etc.) with appropriate changes to the formulas used in the method.

At 502, the minimum required vacuum capacity is determined. The minimum required vacuum capacity (e.g. HP, flow rate (cfm)) is determined by the minimum requirements to capture a satisfactory percentage of generated particles at the source. This determines the size of vacuum source needed. In some implementation, the system may already be in place and the vacuum capacity may be determined by the installed system. Particle capture efficiency can be determined by testing and the flow measured via pitot tube, anemometer, etc. An extension tube from the source may be used to provide constant flow and diameter for determining acceptable flow.

The instruments used for testing are identified at 504. Instruments are selected based on desired output, e.g. particle count distribution, particle mass distribution, etc. Some instruments have fixed flow rates for all ranges. Others may adapt to different flow rates for different analysis ranges. For example, one known portable aerosol spectrometer outputs particle size concentration and particle mass distribution and requires an air flow of 1.2 liters per minute (lpm). A known ultrafine particle counter requires an airflow of 0.7 lpm. Another known aerosol monitor measures mass concentrations of particles and requires an airflow between 1.5-8 lpm, depending on particle size range. Some known cascade impactors require a flow of 9 lpm. Given the variability on the flow requirements for different detection instruments, the particular data desired and the particular instruments to be used to acquire that data must be determined in order to determine the air flow requirements.

At 506, the method includes determining the sampling duct (e.g. sampling tower 218) diameter. The diameter is determined based on the number of sampling probes to be used, including pitot tubes, vacuum source flow rate, and the available pipe/tube sizes for the sampling tower. Depending on the instruments selected, a target velocity in the duct may be between approximately 2 and 25 lpm. Should any manufacturer have an existing isokinetic nozzle, the velocity may be targeted for that nozzle. Duct diameter is generally determined by:

$$Q = VA \tag{1}$$

where Q=flow rate, V=velocity, A=area, and by:

$$A = \pi D^2 / 4 \tag{2}$$

where D is the duct diameter. The selected diameter also needs to be large enough that there is sufficient clearance for the nozzles/tubes in the duct.

The length of sampling tower 218 is determined at 508. The length is determined based on required, recommended, or desired ratios of upstream and downstream requirements for nozzles 220 and/or other sensors, detectors, etc. For example, pitot tubes have a minimum required ratio of upstream and downstream sections with longer sections desired for greater accuracy. The location of placement of nozzles 220 in sampling tower 218 may also affect the length of the sampling tower. As a rule of thumb, sampling nozzles 220 should not be closer to the inlet of sampling tower 218 than four times the diameter of sampling tower 218. If the system is intended to be portable, the length of sampling tower 218 should be kept as short as possible, while still meeting the requirements of the nozzles 220 and other devices, to facilitate moving the sampling tower 218 between particle producing devices.

At 510 the diameters for nozzle holes are determined based on the instruments selected, the sampling tower diameter, and the target velocity in the sampling tower. For isokinetic conditions, nozzle diameters are calculated from equations (1) and (2) above, where V is the nozzle velocity and the velocity in the sampling tower, Q is the required flow rate of the instrument to which the nozzle will be coupled, and D is the diameter of the nozzle hole.

Figure 6:
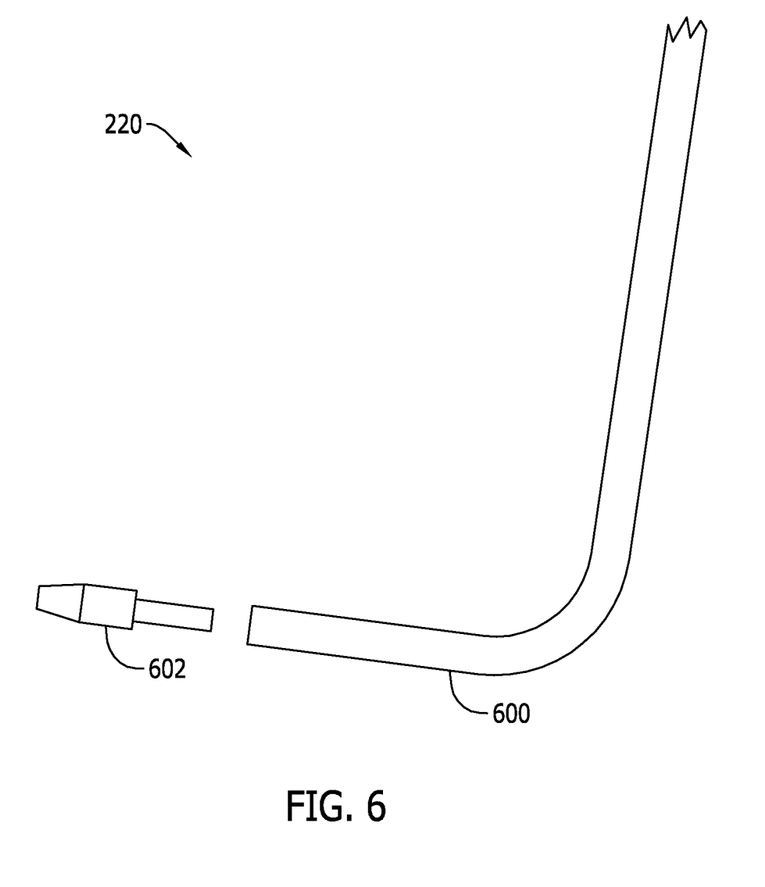
FIG. 6 is a view of a disassembled nozzle for use in the systems shown in FIGS. 2, 3, and/or 4.

The nozzle tubes and nozzle tube outer diameters are determined at 512. FIG. 6 is a view of an example nozzle 220. As shown in FIG. 6, nozzles 220 include a tube 600 and a tip 602 that is attached to the tube. For maximum flexibility and portability, nozzle tips are designed to be interchangeable. This is accomplished by using a threaded nozzle tip. The diameter of the nozzle tubes are sized from the nozzle hole diameter determined at 510, the available minor and major thread diameters, and the available tubing sizes. In the exemplary implementation, for nozzles 220 (including tubes 600 and tips 602) are made of 316 stainless steel. Alternatively, nozzles 220 may be made of any suitable material. The nozzle hole (i.e., the hole in the nozzle tip) should be smaller than the minor diameter of the thread and the major diameter of the thread must fit into the nozzle tube. The nozzle tube diameter should be kept as small as possible to limit interference with the particles in the sampling tower.

Figure 7:
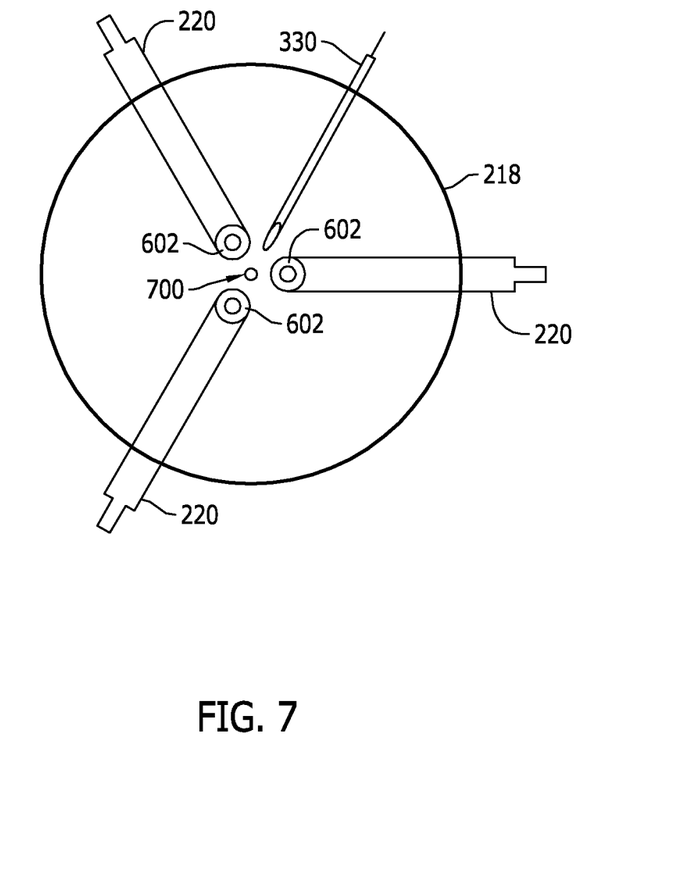
FIG. 7 is a cross-sectional view of the sampling tower shown in FIG. 3.

The arrangement of nozzles 220 within sampling tower 218 is determined at 514. FIG. 7 is a cross sectional view of sampling tower 218 taken along the line A-A shown in FIG. 3. Nozzles 220 and pitot tube 330 are arranged in sampling tower 218 staggered around the circumference of the sampling tower 218 to avoid interference to particle flow. Nozzles 220 should be arranged to permit maximum flow in sampling tower 218 and should have the tips 602 positioned as close as possible to the center 700 of the sampling tower 218. Nozzles 220 may be spaced longitudinally (e.g., along length 221 shown in FIGS. 2 and 3) along sampling tower 218. An upstream nozzle 220 should not block a downstream nozzle 220, which can happen if they are staggered around the circumference of the sampling tower 218.

At 516, if further optimization is desired, method 500 returns to 502 after the arrangement of nozzles 220 has been determined. When further optimization is not desired, the purge air source is selected at 518. A purge air source (e.g., blower 214) may be, for example, a blower from a shop vacuum, a dedicated blower, etc. The selected purge air source should be capable of providing at least as much air as is being withdrawn from enclosure 206 by the selected vacuum source.

If the designed system is intended to be a portable system, the system design may need to be adjusted when the system is moved to a different device. To use the same isokinetic sampling tower 218 for a particle producing device 202 other than the particle producing device 202 for which it was designed, the velocity in the sampling tower 218 when connected to the new particle producing device 202 is calculated or measured, such as by use of pitot tubes and a differential pressure gage. Once the new sampling tower 218 velocity is known, the nozzle tips 602 on the nozzle tubes 600 can be replaced (if the new velocity differs from the old velocity) with nozzle tips 602 that result in the velocity in the nozzle being equal to the new velocity in the sampling tower 218. The new tips 602 may be selected as described at 510. If the new velocity differs from the original velocity, a new purge air source may need to be selected, or the source may need to be adjusted, as described with reference to 518.

The exemplary systems and methods described herein permit quantification and characterization of substantially all of the particles produced by a particle producing device. Accurately quantifying, the size, distribution, and quantities of particles produced from manufacturing aids the study of processing techniques and health and safety. Understanding the size, count, and distribution of total particles produced can help improve efficiency of capture, optimize cutting tool design, study new material systems, and create productive and safe processes. The exemplary systems work for nearly any process where dust can be captured by vacuum and are portable and adaptable to a variety of machines (including mobile machines), cutting tools, processes, materials. The systems can use a wide variety of detection/sampling instrumentation. The exemplary systems have relatively low costs and are relatively easy to setup. The use of filtered air as a purge helps limit contaminants to ensure that only particles produced by the device being studied are analyzed. Moreover, the exemplary systems can coupled to existing vacuum lines and/or existing dust extraction systems to minimize disturbance to existing systems, simplify installation, enhance system portability, and minimize costs. Through use of the methods and systems described herein, it is possible to understand and characterize particles produced from material removal processes. The knowledge about the particles produced may be useful for protecting worker health and safety, minimizing environmental impact, improving cutting tool design, improving the removal process (e.g., the order of steps, depth of cut per pass, etc.), and improving dust extraction system design. Use of the exemplary systems provides an improved understanding of material fracture under different processing conditions through particle analysis. Possible safety concerns regarding new material systems and efficiencies of new machines may be studied, and the understanding of current systems may be improved. The exemplary systems permit new standards for new material systems or changes to existing standards to be quantitatively addressed. Moreover, the systems may be used for real time monitoring for the deliberate production of particles (e.g. reinforcements, fillers, etc.). Further, closed version of the described systems may be useful for monitoring and/or controlling processes involving hazardous or potentially hazardous materials.

It should be appreciated that one or more aspects of the present disclosure may transform a general-purpose computing device into a special-purpose computing device when configured to perform the functions, methods, and/or processes described herein.

This written description uses examples to disclose various implementations, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for use in particle collection and analysis, said system comprising:
    an enclosure configured to be attached to a particle-producing device that will produce particles at a particle generation location during operation of the particle-producing device, said enclosure including an inlet and an outlet including an adjustable nozzle positionable close to the particle generation location when the enclosure is attached to the particle-producing device;

a filter configured to be coupled to the inlet of said enclosure and configured to filter air directed to said enclosure through the inlet;

a vacuum source configured to be coupled in flow communication with the outlet of said enclosure to generate a stream from said enclosure to said vacuum source, wherein the stream comprises a flow of air and particles produced by the particle producing device during operation of the particle-producing device when the enclosure is attached to the particle-producing device; and a sampling tower configured to be coupled between said vacuum source and said enclosure outlet, said sampling tower including at least one sampling nozzle extending into said sampling tower and configured for sampling the stream from said enclosure to said vacuum source.

2. The system of claim 1, further comprising a blower configured to be coupled to said filter to provide filtered air to said enclosure.

3. The system of claim 2, wherein said blower is configured to provide air to said enclosure at substantially a same rate as said vacuum source is configured to extract air from said enclosure.

4. The system of claim 1, wherein said at least one sampling nozzle comprises an isokinetic sampling nozzle.

5. The system of claim 4, further comprising a detection instrument configured to detect at least one characteristic of the particles included in the stream.

6. The system of claim 5, further comprising a computing device configured to be communicatively coupled to said detection instrument to receive from said detection instrument data about the detected characteristic of the particles included in the stream.

7. The system of claim 5, wherein said instrument is one of a cascade impactor, a particle counter, a mass concentration monitor, and a single stage impactor.

8. The system of claim 4, wherein said sampling tower further comprises a pitot tube coupled to a differential pressure gauge to detect the velocity of the stream in said sampling tower.

9. The system of claim 1, wherein said vacuum source includes a blower outlet configured to be coupled to said filter to provide filtered air to said enclosure.

10. The system of claim 1, wherein said enclosure is configured to maintain said adjustable nozzle in a substantially fixed location relative to the particle generation location.

11. The system of claim 1, wherein said enclosure is configured to provide a substantially sealed volume around the particle generation location when said enclosure is attached to the particle-producing device.

12. A method for collection and analysis of particles from a particle-producing source enclosed within an enclosure having an inlet and an outlet, said method comprising:

supplying filtered air into the enclosure through the inlet at an input flow rate;

extracting, with a vacuum source, a stream comprising a flow of air and particles from the particle-producing source through the outlet at an output flow rate approximately equal to the input flow rate;

directing the stream from the outlet of the enclosure to the vacuum source via a sampling tower, the sampling tower including at least one nozzle for sampling the stream;

detecting, with a detection instrument coupled to the nozzle, at least one characteristic of the particles in the stream; and outputting data concerning the detected characteristic of the particles in the stream to a computing device.

13. The method of claim 12, further comprising:

determining a velocity of a sample stream through the sampling tower;

determining, based at least in part on the determined velocity of the sample stream, a size of the at least one nozzle such that a velocity in the at least one nozzle substantially equals the determined velocity; and installing the at least one nozzle with the determined size in the sampling tower.

14. The method of claim 12, wherein the particle-producing source is part of a particle-producing device, and wherein said method further comprises:

affixing the enclosure to the particle-producing device such that the enclosure substantially encloses the particle-producing source, wherein the enclosure comprises a flexible membrane.

15. The method of claim 12, wherein the sampling tower includes a plurality of nozzles for sampling the stream, and wherein said detection instrument coupled to the nozzle detects a plurality of characteristics of particles in the stream.

16. The method of claim 15, wherein the sampling tower has a substantially circular cross section and wherein said method further comprises positioning the plurality of nozzles in the sampling tower staggered in a circumferential direction around the sampling tower.

17. A system for use in collection and analysis of particles produced at a particle-producing location of a particle-producing device, said system comprising:

an enclosure attached to a particle-producing device, said enclosure and the particle-producing device cooperatively creating a substantially sealed volume around the particle-producing location, said enclosure including an inlet to the sealed volume and an outlet from the sealed volume;

a filter coupled to the inlet of said enclosure and configured to filter air directed to said enclosure through the inlet;

a first vacuum source having an inlet and an outlet, said first vacuum source inlet coupled in flow communication with said enclosure outlet to generate an stream from said enclosure to said first vacuum source, wherein the stream comprises a flow of air and particles produced by the particle-producing device, and wherein said first vacuum source outlet is coupled in flow communication with said filter to provide filtered air to said enclosure; and a sampling tower coupled between said first vacuum source inlet and said enclosure outlet, said sampling tower including a plurality of sampling nozzles extending into said sampling tower and configured for sampling the stream from said enclosure to said vacuum source.

18. The system of claim 17, further comprising a second vacuum source having an inlet and an outlet, wherein said second vacuum source inlet is coupled in flow communication with a volume outside said enclosure and said second vacuum source outlet is coupled in flow communication with said filter to provide filtered air to said enclosure.

19. The system of claim 17, further comprising a plurality of detection instruments coupled to the plurality of nozzles, wherein each detection instrument is configured to detect at least one characteristic of the particles in the stream.

20. The system of claim 17, wherein said enclosure is configured to maintain said enclosure outlet in a substantially fixed position relative to said particle producing location.

* * * * *